United States Patent [19]

McArthur et al.

[11] Patent Number: 4,929,628
[45] Date of Patent: May 29, 1990

[54] OXADIAZOLE COMPOUNDS, THEIR PREPARATION AND THEIR USE AS PESTICIDES

[75] Inventors: Alastair McArthur; Royston H. Davis; Mark D. Hilton; Trevor W. Newton; Dinesh M. Patel, all of Sittingbourne, England

[73] Assignee: Shell Internationale Research Maatschappij, B. V., The Hague, Netherlands

[21] Appl. No.: 298,691

[22] Filed: Jan. 19, 1989

[30] Foreign Application Priority Data

Jan. 21, 1988 [GB] United Kingdom ................ 8801289

[51] Int. Cl.$^5$ .................... C07D 271/06; A01N 43/26
[52] U.S. Cl. ...................................... 514/364; 548/132
[58] Field of Search ......................... 548/132; 514/364

[56] References Cited

U.S. PATENT DOCUMENTS 4,694,014 9/1987 Beriger .............................. 514/363

FOREIGN PATENT DOCUMENTS 0036711 8/1981 European Pat. Off. ............ 548/132
0217747 4/1987 European Pat. Off. ............ 548/132
2426878 1/1976 Fed. Rep. of Germany ...... 548/132

OTHER PUBLICATIONS

Fuchigami, T., et al., Bulletin of the Chemical Society of Japan, 49(12), 3607–3610 (1976)–In English.
Martin, D., et al., Chemische Berichte, 99(1), 317–327 (1966), In German.
Eloy, Chim. Ther. 1969, 4 pp. 9–13.

Primary Examiner—Robert Gerstl

[57] ABSTRACT

The invention provides 1,2,4-oxadiazole compounds of general formula

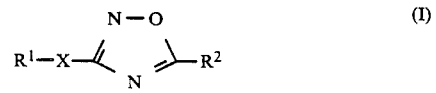

(I)

wherein $R^1$ represents an optionally substituted phenyl group, $R^2$ represents an optionally substituted phenyl group and X represents an oxygen or sulphur atom; processes for their preparation and their use as pesticides, particularly as acarid ovicides.

9 Claims, No Drawings

OXADIAZOLE COMPOUNDS, THEIR PREPARATION AND THEIR USE AS PESTICIDES

This invention relates to oxadiazole compounds, to processes for their preparation, and to the use of such compounds as pesticides.

EP-A-No. 36711 discloses a broad class of compounds of the formula

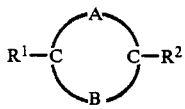

wherein $R^1$ represents phenyl substituted in at least the 2-position by fluorine, chlorine, bromine or iodine, $R^2$ represents a group $R^3$, $-OR^3$, $-SR^3$ or $-NR^3R^4$ where $R^3$ represents hydrogen, alkyl of 1 to 6 carbon atoms, cycloalkyl of 3 to 7 carbon atoms, alkenyl of 2 to 6 carbon atoms, cycloalkenyl of 3 to 7 carbon atoms, alkynyl of 2 to 6 carbon atoms, phenyl, phenylalkyl of 7 to 10 carbon atoms or naphthyl, each of which may be unsubstituted or substituted by one or more halogen atoms, alkyl or alkoxy or alkylthio groups of 1 to 6 carbon atoms, nitro groups, cyano groups or mercapto groups, $R^4$ represents a group as defined for $R^3$ but not necessarily identical thereto, and A and B, together with the carbon atoms to which they are attached, form a 3,6-disubstituted pyridazine, a 3,6-disubstituted dihydropyridazine, a 2,5-disubstituted pyrimidine, a 1,2,4-oxadiazole, a 1,2,4-oxadiazoline or a 1,2,4-triazole ring, and the quaternary salts thereof. It is specifically recited that $R^2$ preferably represents a group $R^3$, especially a cycloalkyl group of 5 or 6 carbon atoms, e.g. cyclohexyl, or a phenyl group which is desirably substituted by one or more halogen atoms, $C_{1-4}$ alkyl or alkoxy groups or nitro groups. It is further stated that $R^1$ and $R^2$ are preferably identical. The compounds are disclosed as of general use as insecticides, acaricides, aphicides, larvicides and/or ovicides.

The only oxadiazoles disclosed in EP-A-No. 36711 are 3,5-bis(2-chlorophenyl)-1,2,4-oxadiazole, 3-(2-chlorophenyl)-5-cyclohexyl-1,2,4-oxadiazole, 3-(2-chlorophenyl)-5-hydroxy-1,2,4-oxadiazole and 5-(2-chlorophenyl)-3-cyclohexyl-1,2,4-oxadiazole.

Martin and Weise, Chemische Berichte 99(1), 317 to 327 (1966) discloses 5-phenoxy-2-phenyl-1,3,4-oxadiazole and 5-para-tolyloxy-2-phenyl-1,3,4-oxadiazole, described as being produced respectively by heating 5-phenoxy-2-benzoyl tetrazole, and its para-tolyloxy analogue, under reflux in dimethylformamide. The 5-phenoxy-2-benzoyltetrazole (and the tolyloxy analogue) was produced and isolated by reaction of 5-phenoxytetrazole with benzoylchloride in benzene together with triethylamine, the benzene being evaporated off after removal of precipitated triethylamine hydrochloride. There is no disclosure of any utility for the 1,3,4-oxadizoles.

It has now been discovered that a certain class of 1,2,4-oxadizoles exhibits surprisingly effective pesticidal, particularly acarid ovicidal activity.

According to the present invention there are provided 1,2,4-oxadiazole compounds of general formula

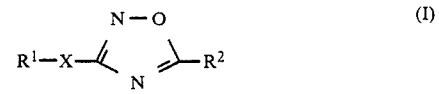

wherein $R^1$ represents an optionally substituted phenyl group, $R^2$ represents an optionally substituted phenyl group and X represents an oxygen or sulphur atom.

Optional substituents in optionally substituted phenyl groups include for example halogen atoms, cyano, nitro, alkyl, haloalkyl, alkoxy, haloalkoxy, and hydroxyiminoalkyl groups. Alkyl or substituted alkyl moieties preferably contain 1 to 6, more preferably 1 to 4, carbon atoms. Preferred compounds of formula I comprise those compounds having one or more of the following features:

(i) $R^1$ represents a phenyl group optionally substituted by one to three substituents independently selected from halogen atoms, $C_{1-6}$ alkoxy groups and $C_{1-6}$ hydroxyimino alkyl groups, (ii) the phenyl group represented by $R^1$ is substituted in the 4-position by a $C_{1-4}$ alkoxy group, (iii) $R^1$ represents a phenyl group substituted in the 4-position by a methoxy or ethoxy group, (iv) $R^2$ represents a phenyl group optionally substituted by one to three substituents independently selected from halogen atoms, $C_{1-6}$ alkoxy groups and nitro groups, (v) the phenyl group represented by $R^2$ is substituted in the 2-position by a halogen atom, (vi) $R^2$ represents a phenyl group substituted in the 2-position by a fluorine, chlorine or bromine atom, and (vii) X represents an oxygen atom.

Preferred combinations of the above features include (i), (iv) and (vii); (i),(ii),(iv),(v) and (vii); and most preferably (iii), (vi), and (vii).

The invention further provides a process for the preparation of a compound of general formula I as defined above which comprises reacting a compound of formula

wherein $R^1$ and X are as defined above and $R^3$ represents a hydrogen atom and $R^4$ represents an amino group or an acid adduct thereof or $R^3$ and $R^4$ together with the interjacent carbon and nitrogen atoms represent a tetrazolyl group with a compound of formula

wherein $R^2$ is as defined above and L represents a leaving group, followed in the case wherein $R^3$ represents a hydrogen atom and $R^4$ represents an amino group or an acid adduct thereof by treatment with a halogenating agent followed by treatment with a base, to produce the compound of formula I.

L represents a leaving group, e.g. a bromine or, preferably, a chlorine atom. The halogenating agent is preferably an alkyl hypochlorite, e.g. t-butyl hypochlorite.

Reaction of the compound of formula II wherein $R^3$ and $R^4$ together with the interjacent carbon and nitrogen atoms represents a tetrazolyl group with the compound of formula III may be effected in the presence of an aprotic solvent such as benzene, toluene, xylenes, chlorinated hydrocarbons, diethyl ether, tetrahydrofuran, dioxan or acetone. Triethylamine may be included if desired. The reaction may very conveniently be effected at the reflux temperature of the reaction mixture.

5-Phenoxytetrazole and its preparation are described by Martin and Weise, Chemische Berichte 99(1), 317 to 327 (1966), and other compounds of formula II wherein $R^3$ and $R^4$ together with the interjacent carbon and nitrogen atoms represent a tetrazolyl group may be prepared in analogous manner.

Reaction of the compound of formula II wherein $R^3$ represents a hydrogen atom and $R^4$ represents an amino group or an acid adduct thereof with the compound of formula III may conveniently be effected in the presence of an aprotic solvent such as benzene, toluene, xylenes, chlorinated hydrocarbons (e.g. chloroform), diethyl ether, tetrahydrofuran, dioxan or acetone and of a base, e.g. triethylamine, conveniently at a temperature of in the range $-10°$ C. to $50°$ C. preferably $0°$ to $5°$ C.

The resulting product is an N-benzoyl-O-phenylisourea of general formula $R^1.X.C(NH).NH.CO.R^2$. The subsequent treatment of this isourea product with the halogenating agent may conveniently be effected in a non-aqueous protic solvent, e.g. a $C_{1-6}$ alkanol such as ethanol or methanol, at a temperature in the range $0°$ to $10°$ C. The subsequent treatment with a base may then conveniently be effected by addition to the reaction mixture of an aqueous solution of an alkali metal hydroxide, e.g. sodium hydroxide or potassium metal hydroxide, at a temperature in the range $0°$ to $100°$ C. ambient temperature being very convenient.

The compound of formula II wherein $R^3$ represents a hydrogen atom and $R^4$ represents an amino group may be prepared by reaction of a compound of formula $R^1XH$ with chloroamidine hydrochloride $(Cl.C(NH).NH_2.HCl)$, conveniently without solvent at a temperature in the range $120°$ to $150$ C.

Compounds of formula III are benzoic acid derivatives, which are either known compounds or may be prepared by methods analogous to those used for preparing the known compounds.

The compounds of the general formula I exhibit pesticidal, especially acarid ovicidal, activity. Accordingly the invention also provides a pesticidal composition comprising a carrier and, as active ingredient, a compound of general formula I. The invention further provides a method of combating pests at a locus, which comprises treating the locus with a pesticidal compound or composition according to the invention, and specifically provides the use as an acarid ovicide of a compound of general formula I.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating pesticidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montomorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3-10% w of a dispersing agent and, where necessary, 0-10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½-10% w of active ingredient. Granules are usually prepared to have a size between 10 and 100 BS mesh (1.676-0.152 mm), and may be manufactured by agglomeration or impregnation techniques. Generally, granules will contain ½-75% w active ingredient and 0-10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension conentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

Compositions in accordance with the invention may also contain other ingredients, for example other compounds possessing pesticidal, herbicidal, or fungicidal properties. The compounds of the invention may be found to be especially useful when applied in admixture with other insecticides and/or acaricides, e.g. organophosphates, pyrethroids, ureas and organotin compounds, for example the commercial products fenvalerate, permethrin, cypermethrin, deltamethrin, alphacypermethrin, fenbutatin oxide, flufenoxuron, diflubenzuron and trefluron.

The invention will be further understood from the following examples.

EXAMPLE 1

Preparation of 3-(4-methoxyphenoxy)-5-(2-fluorophenyl)-1,2,4-oxadiazole

To a solution of 4-methoxyphenol (25 g, 201 mmol) in acetone (100 ml) was added, with stirring, sodium bicarbonate (16.9 g, 201 mmol) and cyanogen bromide (21.35 g, 201 mmol). The mixture was cooled to 0° C. and triethylamine (20.34 g, 201 mmol) was added dropwise. After addition of triethylamine was complete, the mixture was stirred at ambient temperature (20° C.) for a further two hours.

The resulting mixture was cooled to 0° C. and a solution of sodium azide (13.1 g, 201 mmol) and sodium bicarbonate (1 g) in water (30 ml) was added dropwise. When addition was complete, the resulting mixture was stirred for 8 hours at ambient temperature (20° C.). The acetone was then evaporated off under reduced pressure and the residue was acidified by addition of concentrated nitric acid (25 ml). The precipitate which separated out was filtered off and washed with dichloromethane to give 4-methoxyphenoxy tetrazole (32.5 g), m.p. 150.2° C.

To a solution of the 4-methoxyphenoxy tetrazole (1 g, 5.2 mmol) in dry benzene (30 ml) was added, with stirring, 2-fluorobenzoylchloride (0.83 g, 5.2 mmol). The resulting mixture was heated under reflux for 8 hours, cooled and washed with cold (0° C.) 10% w/v aqueous sodium hydroxide solution. Benzene was evaporated off under reduced pressure to leave the crude product as a white solid, which was purified over silica gel using chloroform as eluant to give 2-(4-methoxyphenoxy)-5-(2-fluorophenyl)-1,2,4-oxadiazole as a white solid (0.6 g, 40%), m.p. 99.1° C.

Analysis: $C_{15}H_{11}N_2O_3F$: C 62.9; H 3.9; N 9.8 Found: C 62.9; H 3.9; N 9.7

EXAMPLE 2

Preparation of 3-phenoxy-5-phenyl-1,2,4-oxadiazole

Hydrogen chloride gas was bubbled into a solution of cyanamide (15 g) in diethylether (340 ml) at 0° C. for 1½ hours. Chloroamidine hydrochloride was filtered off as a white solid.

Chloroamidine hydrochloride (10 g) was added to phenol (100 g) at 60° C., and the mixture was heated to 140° C. and stirred for two hours. The mixture was then allowed to cool to ambient temperature (20° C.), and the resulting mass was washed with acetone and diethylether to leave O-phenylisourea hydrochloride as a white solid (7.0 g), m.p. 171.5° C.

O-phenylisourea (1 g) was dissolved in chloroform (50 ml) and triethylamine (1.2 g) and thereafter benzoylchloride (0.8 g) were added at 0° to 5° C. After stirring for one hour at 0° to 5° C., the mixture was washed with water and the chloroform was evaporated off under reduced pressure to give N-benzoyl-O-phenylisourea (1 g), m.p. 125.1° C.

N-benzoyl-O-phenylisourea (0.8 g) was dissolved in ethanol (40 ml), and t-butylhypochlorite (0.36 g) was added at 0° to 5° C. After one hour, 2 molar aqueous sodium hydroxide (2 ml) was added and the mixture was stirred for 2 hours at ambient temperature (20° C.). The reaction mixture was poured into an equal volume of water and extracted with dichloromethane (100 ml). The separated organic layer was evaporated under reduced pressure and the residue was purified by chromatography over silica gel using dichloromethane as eluant to give 3-phenoxy-5-phenyl-1,2,4-oxadiazole (0.4 g, 57%), m.p. 62° C.

Analysis: $C_{14}H_{10}N_2O$: Calc.: C 70.6; H 4.2; N 11.8 Found: C 70.3; H 4.2; N 11.8

EXAMPLES 3 TO 26

By processes similar to that of Example 1 were prepared a number of other compounds of the invention, as detailed in Table I following:

TABLE 1

$$Y^1 - \text{C}_6\text{H}_3(Y^2) - O - C(=N-O-\text{C}_6\text{H}_2(Z^1)(Z^2)(Z^3)) - N$$

| Example | Y¹ | Y² | Z¹ | Z² | Z³ | M.p. (°C.) (or IR) | Yield (%) | | C | H | N |
|---|---|---|---|---|---|---|---|---|---|---|---|
| 3 | H | H | Cl | H | H | 53.9 | 62.7 | Calc. | 61.7 | 3.3 | 10.3 |
|   |   |   |   |   |   |      |      | Found | 61.9 | 3.4 | 11.5 |
| 4 | H | H | F | H | F | 79.5 | 100 | Calc. | 61.3 | 3.0 | 10.2 |
|   |   |   |   |   |   |      |     | Found | 61.3 | 3.0 | 10.3 |
| 5 | H | H | NO₂ | H | H | 176.5 | 68.4 | Calc. | 59.4 | 3.2 | 14.8 |
|   |   |   |     |   |   |       |      | Found | 59.4 | 3.2 | 14.9 |
| 6 | H | F | Cl | H | H | 83.5 | 100 | Calc. | 57.8 | 2.8 | 9.6 |
|   |   |   |    |   |   |      |     | Found | 57.6 | 3.5 | 10.2 |
| 7 | CH₃O | H | I | H | H | 84.8 | 63.5 | Calc. | 45.7 | 2.8 | 7.1 |
|   |      |   |   |   |   |      |      | Found | 45.7 | 2.8 | 7.2 |
| 8 | H | H | I | H | H | oil (lambda = 1600, 1580, 1200 cm⁻¹) | 68.7 | Calc. | 46.2 | 2.5 | 7.7 |
|   |   |   |   |   |   |                                        |      | Found | 46.9 | 2.6 | 7.7 |
| 9 | H | H | F | H | H | 50.9 | 76 | Calc. | 65.6 | 3.5 | 11.0 |
|   |   |   |   |   |   |      |    | Found | 66.3 | 3.6 | 11.0 |
| 10 | H | H | Br | H | H | oil (lambda = 1605, 1590, 1200 cm⁻¹) | 96 | Calc. | 53.0 | 2.8 | 8.8 |
|    |   |   |    |   |   |                                        |    | Found | 53.3 | 3.0 | 9.1 |
| 11 | H | H | H | CH₃O | H | 92.2 | 41 | Calc. | 67.2 | 4.5 | 10.4 |
|    |   |   |   |      |   |      |    | Found | 67.0 | 4.6 | 10.5 |
| 12 | C₂H₅O | H | F | H | H | 73.9 | 36.4 | Calc. | 64.0 | 4.4 | 9.3 |
|    |       |   |   |   |   |      |      | Found | 63.3 | 4.3 | 9.1 |
| 13 | CH₃O | H | H | H | H | 84.2 | 30.1 | Calc. | 67.2 | 4.5 | 10.4 |
|    |      |   |   |   |   |      |      | Found | 66.7 | 4.5 | 10.4 |
| 14 | CH₃CH₂O | H | H | H | H | 123.5 | 30.7 | Calc. | 68.1 | 5.0 | 9.9 |
|    |         |   |   |   |   |       |      | Found | 67.7 | 5.2 | 9.8 |
| 15 | HON=CH | H | CH₃O | H | H | 100.5 | 28.3 | Calc. | 62.8 | 4.7 | 12.9 |
|    |        |   |      |   |   |       |      | Found | 62.8 | 4.8 | 13.1 |
| 16 | CH₃ | H | Cl | H | H | 79.8 | 46.1 | Calc. | 62.8 | 3.9 | 9.8 |
|    |     |   |    |   |   |      |      | Found | 61.8 | 3.8 | 9.5 |
| 17 | CH₃O | H | Cl | H | H | 86.3 | 81.7 | Calc. | 59.5 | 3.7 | 9.3 |
|    |      |   |    |   |   |      |      | Found | 59.6 | 3.8 | 9.4 |
| 18 | C₂H₅O | H | Cl | H | H | 68.5 | 39.1 | Calc. | 60.7 | 4.1 | 8.8 |
|    |       |   |    |   |   |      |      | Found | 59.8 | 4.1 | 8.9 |
| 19 | CH₃O | H | F | H | F | 101.2 | 31.6 | Calc. | 59.2 | 3.3 | 9.2 |
|    |      |   |   |   |   |       |      | Found | 57.8 | 3.1 | 9.6 |
| 20 | CH₃O | H | F | F | H | 134.5 | 50 | Calc. | 59.2 | 3.3 | 9.2 |
|    |      |   |   |   |   |       |    | Found | 59.5 | 3.5 | 9.3 |
| 21 | CH₃(CH₂)₂O | H | F | H | H | 83 | 25.6 | Calc. | 65.0 | 4.8 | 8.9 |
|    |            |   |   |   |   |    |      | Found | 65.2 | 4.9 | 8.9 |
| 22 | CH₃(CH₂)₂O | H | Cl | H | H | 69.1 | 30 | Calc. | 61.7 | 4.6 | 8.5 |
|    |            |   |    |   |   |      |    | Found | 60.9 | 4.3 | 7.1 |
| 23 | CH₃(CH₂)₃O | H | F | H | H | 49.8 | 33.2 | Calc. | 65.9 | 4.9 | 8.5 |
|    |            |   |   |   |   |      |      | Found | 66.5 | 5.5 | 8.7 |
| 24 | CH₃(CH₂)₃O | H | Cl | H | H | 55.1 | 44.5 | Calc. | 62.7 | 5.0 | 8.1 |
|    |            |   |    |   |   |      |      | Found | 62.8 | 5.0 | 8.1 |
| 25 | C₂H₅O | H | Br | H | H | 71.2 | 12.9 | Calc. | 53.2 | 3.6 | 7.8 |
|    |       |   |    |   |   |      |      | Found | 53.6 | 3.7 | 7.9 |
| 26 | H | H | H | H | H | 62 | 80 | Calc. | 70.6 | 4.2 | 11.8 |
|    |   |   |   |   |   |    |    | Found | 70.3 | 4.2 | 11.8 |

EXAMPLE 27

Acarid Ovicidal Activity

The acarid ovicidal activity of compounds of the invention was assessed using eggs of the glasshouse red spider mite, *Tetranychus urticae* Koch (T.u.Ov.) by the following procedure.

Glasshouse red spider mites are reared on French bean plants at 20° C. Leaf discs (2 cm diameter) are cut from the leaves of French bean plants and are held on 5.5 cm filter paper kept moist by a cotton wool wick dipping into water. Each leaf disc is infested with ten adult mites. After 24 hours the mites are removed and the number of eggs laid is counted (averages approximately 70 eggs).

The leaf discs are sprayed using a logarithmic spraying machine with a solutuion or supension of the test compound, initially at a concentration of 0.1% w in water containing 10% w acetone and 0.025% "TRITON X-100" (trade mark) surface-active agent (the condensation product of ethylene oxide with an alkyl phenol), and subsequently with a series of half-dilutions, at a spray rate equivalent to 340 liters per hectare.

After 7 days under glasshouse conditions (23°±2° C., fluctuating humidity and light), the numbers of hatched nymph and unhatched eggs are counted and the percentage mortality calculated.

In each case an LC$_{50}$ (the concentration of active material required to kill half of the test species) was calculated from the percentage mortality results and compared with the corresponding LC$_{50}$ for a standard miticide, chlorfenson (4-chlorobenzenesulphonic acid 4-chlorophenyl ester). The results are expressed as toxicity indices, where $$\text{toxicity index} = \frac{LC_{50} \text{ (chlorfenson)}}{LC_{50} \text{ (test compound)}} \times 100$$

and are set out in Table II below.

TABLE II

| Compound of Example No. | Acarid ovicidal activity Toxicity index (T.u.Ov) |
|---|---|
| 1 | 5100 |
| 2 (26) | 750 |
| 3 | 930 |
| 4 | 300 |
| 5 | 171 |
| 6 | 89 |
| 7 | 350 |
| 8 | 99 |
| 9 | 2100 |
| 10 | 1100 |
| 11 | 130 |
| 12 | 4800 |
| 13 | 1100 |
| 14 | 740 |
| 15 | 520 |
| 16 | 104 |
| 17 | 8000 |
| 18 | 4200 |
| 19 | 4600 |
| 20 | 1100 |
| 21 | 1400 |
| 22 | 1100 |
| 23 | 350 |
| 24 | 520 |
| 25 | 4200 |
| Comparative A | 73 |

Comparative A is Example 56 of EP-A-No. 36711, i.e. 3,5-bis(2-chlorophenyl)-1,2,4-oxadiazole, m.p. 91° C.

I claim;

1. A 1,2,4-oxadiazole compound of the general formula

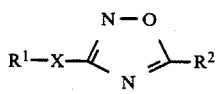

(I)

wherein
R$^1$ is a group selected from phenyl and phenyl substituted by one to three substituents independently selected from halogen atoms, C$_{1-6}$ alkoxy groups and C$_{1-6}$ hydroxyimino alkyl groups,
R$^2$ is a group selected from phenyl and phenyl substituted by one to three substituents independently selected from halogen atoms, C$_{1-6}$ alkoxy groups and nitro groups, and
X is oxygen.

2. A pesticidal composition exhibiting acaricidal activity comprising a carrier and, as an active ingredient, an acaricidally effective amount of a 1,2,4-oxadiazole compound of the general formula

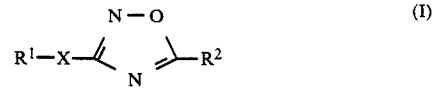

(I)

wherein
R$^1$ is a group selected from phenyl and phenyl substituted by one to three substituents independently selected from halogen atoms, C$_{1-6}$ alkoxy groups and C$_{1-6}$ hydroxyimino alkyl groups,
R$^2$ is a group selected from phenyl and phenyl substituted by one to three substituents independently selected from halogen atoms, C$_{1-6}$ alkoxy groups and nitro groups, and
X is oxygen or sulfur.

3. The composition of claim 2 wherein R$^1$ is phenyl substituted in the 4-position by a C$_{1-4}$ alkoxy group.

4. The composition of claim 3 wherein R$^1$ is a phenyl group substituted in the 4-position by a methoxy or ethoxy group.

5. The composition of claim 2 wherein R$^2$ is a phenyl group substituted in the 2-position by a halogen atom.

6. The composition of claim 5 wherein R$^2$ is a phenyl group substituted in the 2-position by a fluorine, chlorine or bromine atom.

7. The composition of claim 2 wherein X is oxygen.

8. The composition of claim 2 comprising at least two carriers, at least one of which is a surface-active agent.

9. A method of combating acarids at a locus which method comprises treating the locus with a compound of the general formula

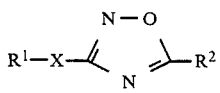

wherein
R$^1$ is a group selected from phenyl and phenyl substituted by one to three substituents independently selected from halogen atoms, C$_{1-6}$ alkoxy groups and C$_{1-6}$ hydroxyimino alkyl groups,
R$^2$ is a group selected from phenyl and phenyl substituted by one to three substituents independently selected from halogen atoms, C$_{1-6}$ alkoxy groups and nitro groups, and
X is oxygen or sulfur.

* * * * *